United States Patent [19]
Takesawa et al.

[11] Patent Number: 5,700,372
[45] Date of Patent: Dec. 23, 1997

[54] DIALYZER WITH A CONSTRICTED PART MADE OF A MATERIAL CAPABLE OF SWELLED BY DIALIZING LIQUID

[75] Inventors: Shingo Takesawa, Tokyo; Noriyuki Hosoya, Kanagawa; Masatomi Sasaki, Kanagawa, all of Japan

[73] Assignee: Terumo Kabushiki Kaisha, Tokyo, Japan

[21] Appl. No.: 523,526

[22] Filed: Sep. 1, 1995

[30] Foreign Application Priority Data

Sep. 2, 1994 [JP] Japan .................. 6-234373

[51] Int. Cl.$^6$ ........................... B01D 63/02
[52] U.S. Cl. ................... 210/321.81; 210/321.6; 210/321.72; 210/321.9; 210/500.23
[58] Field of Search .............. 210/321.6, 321.61, 210/321.65, 321.72, 321.78, 321.79, 321.8, 321.81, 321.87, 321.88, 321.89, 321.9, 500.23; 422/44, 48

[56] References Cited

U.S. PATENT DOCUMENTS

| | | | |
|---|---|---|---|
| 4,187,180 | 2/1980 | Joh | 210/321.81 |
| 4,219,426 | 8/1980 | Spekle et al. | 210/232 |
| 4,293,418 | 10/1981 | Fujii et al. | 210/321.81 |
| 4,367,139 | 1/1983 | Graham | 210/456 |
| 4,376,095 | 3/1983 | Hasegawa | 422/46 |
| 4,657,743 | 4/1987 | Kanno | 422/46 |
| 4,680,122 | 7/1987 | Barone | 210/321.6 |
| 4,923,679 | 5/1990 | Fukusawa et al. | 422/48 |

FOREIGN PATENT DOCUMENTS

| | | |
|---|---|---|
| 0 343 359 | 11/1989 | European Pat. Off. . |
| 0 345 780 | 12/1989 | European Pat. Off. . |
| 52-32200 | 8/1977 | Japan . |
| 56-22911 | 5/1981 | Japan . |

OTHER PUBLICATIONS

"'On Line' Preparation of Sterile Pyrogen–Free Electrolyte Solution", L.W. Hendersonet al., Trans. Am. Soc. Artif. Intern. Organs, vol. 24, pp. 465–467 (1978).

"New Simultaneous HF and HD with No Infusion Fluid", M. Usuda et al., Trans. Am. Soc. Artif. Intern. Organs, vol. 28, pp. 24–27 (1982).

"Characteristics of Removing Low–Molecular Weight Proteins by On–Line Mass Pre–Dilution HDF", Clinical Medicine (1993).

*Primary Examiner*—John Kim
*Attorney, Agent, or Firm*—Burns, Doane, Swecker & Mathis, LLP

[57] ABSTRACT

A dialyzer provided in a cylindrical housing with a bundle of hollow fiber membranes and first flow paths and second flow paths separated from each other by said hollow fiber membranes and allowed to effect dialysis and ultrafiltration through the medium of said hollow fiber membranes between a body liquid flowing through said first flow paths and a dialyzing liquid flowing through said second flow paths, characterized in that a constricted part is formed halfway in the length of said second flow paths with a material capable of being swelled by said dialyzing liquid so as to confer a difference of pressure on said dialyzing liquid on the upstream side and the downstream side of said dialyzing liquid relative to said constricted part.

8 Claims, 3 Drawing Sheets

DIALYZER WITH A CONSTRICTED PART MADE OF A MATERIAL CAPABLE OF SWELLED BY DIALIZING LIQUID

BACKGROUND OF THE INVENTION

1. Field of the Invention

This invention relates to a dialyzer. More particularly, it relates to a hollow fiber membrane type dialyzer to be used for the therapy by blood purification.

2. Description of the Prior Art

In the therapy by blood purification, the method of hemodiafiltration, the method of on-line hemodiafiltration [Henderson, L. W. et al.: Trans. Am. Soc. Artif. Intern. Organs, 24, 465–467 (1978)], and the method of push-and-pull hemodiafiltration [Usuda, M. et al: Trans. Am. Soc. Artif. Intern. Organs, 28, 24–27 (1982)] have been known in the art as means to effect mass displacement between blood and a dialyzing liquid.

The mass displacement of liquids in the method of hemodiafiltration mentioned above necessitates use of a large quantity of a pyrogen-free displacing liquid in addition to the dialyzing liquid. The manufacture of this displacing liquid consumes much labor and time and also incurs high cost because the displacing liquid is expensive.

By contrast, the method of on-line hemodiafiltration mentioned above and the method of push-and-pull hemodiafiltration mentioned above do not suffer the drawbacks mentioned above because they use their dialyzing liquids concurrently as displacing liquids. The method of on-line hemodiafiltration, however, requires a device to be exclusively used for extracting part of the dialyzing liquid from a circuit for the dialyzing liquid and supplying the extracted dialyzing liquid into a circuit for extracorporeal blood circulation. The method of push-and-pull hemodiafiltration requires to be provided midway in the circuit for the dialyzing liquid with a dialyzing liquid supplying and recovering line furnished with a reversible pump and a dialyzing liquid reservoir and branched from the circuit for the purpose of chronologically altering the directions of ultrafiltration of blood and the dialyzing liquid.

These methods, therefore, are invariably at a disadvantage in requiring provision of an extra device of exclusive use and consequently complicating the construction of circuit.

In addition, a dialyzer which has a multiplicity of bundled capillary tubes accommodated in a cylinder and connected at the opposite ends thereof to blood flow mouths of the cylinder, with the inside diameter of the cylinder decreased nearly in the middle of the length thereof so that the capillary tubes are bundled more densely in the part of the decreased inside diameter than in the other parts, has been known in the art (Japan Patent 55-22,911).

The fact that the inside diameter of the cylinder is decreased as described above, however, implies that the overall periphery of the bundle of the hollow fiber membranes is destined to be depressed by hard cylinder ridges defining the part of the decreased inside diameter. This dialyzer, therefore, is at a disadvantage in suffering those hollow fiber membranes bordering on the periphery of the bundle to be deformed under the pressure and the packing ratio of the bundle in the core part thereof (namely, the gaps between the adjacent hollow fiber membranes) to remain unchanged. Further, since the part of the decreased inside diameter renders difficult the insertion of the bundle of hollow fiber membranes into the cylinder, the dialyzer has the further disadvantage that the work of assemblage consumes unduly long time and incurs an increase of cost.

It is thus one object of this invention to provide a novel dialyzer.

It is another object of this invention to provide a dialyzer which permits hemodialysis of mass displacement to be effected with a simple construction without additionally requiring any special device.

It is yet another object of this invention to provide a dialyzer which is assembled readily and therefore manufactured easily.

SUMMARY OF THE INVENTION

The objects mentioned above are accomplished by a dialyzer provided in a cylindrical housing with a bundle of hollow fiber membranes and first flow paths and second flow paths separated from each other by the hollow fiber membranes and allowed to effect dialysis and ultrafiltration through the medium of the hollow fiber membranes between a body liquid flowing through the first flow paths and a dialyzing liquid flowing through the second flow paths, characterized in that a constricted part is formed halfway in the length of the second flow paths with a material capable of being swelled by the dialyzing liquid so as to confer a difference of pressure on the dialyzing liquid on the upstream side and the downstream side of the dialyzing liquid relative to the constricted part.

This invention further concerns the dialyzer mentioned above, wherein the pressure of the dialyzing liquid flowing through the second flow paths is so set as to be higher than that of the body liquid flowing through the first flow paths on the upstream side of the dialyzing liquid relative to the constricted part and the pressure of the dialyzing liquid flowing through the second flow paths is so set as to be lower than that of the body liquid flowing through the first flow paths on the downstream side of the dialyzing liquid relative to the constricted part. This invention further concerns the dialyzer mentioned above, wherein the constricted part is formed by causing a constricted part-forming member to fill the gap between the adjacent hollow fiber membranes. This invention further concerns the dialyzer mentioned above, wherein the dialyzing liquid swellable material has a dialyzing liquid absorption capacity of not less than 10%. This invention further concerns the dialyzer mentioned above, which is additionally provided with ultrafiltration rate (hereinafter referred to UFR) control means for adjusting the amount of water to be removed from the body liquid flowing through the first flow path. This invention further concerns the dialyzer mentioned above, wherein the constricted part-forming member is formed of dialyzing liquid-swellable fibers. This invention further concerns the dialyzer mentioned above, wherein the packing ratio of the hollow fiber membranes in the constricted part is in the range of from 105 to 200% based on the packing ratio in the parts other than the constricted part.

DESCRIPTION OF THE PREFERRED EMBODIMENT

Now, the dialyzer of this invention will be described below with reference to the drawings.

Figure 1:
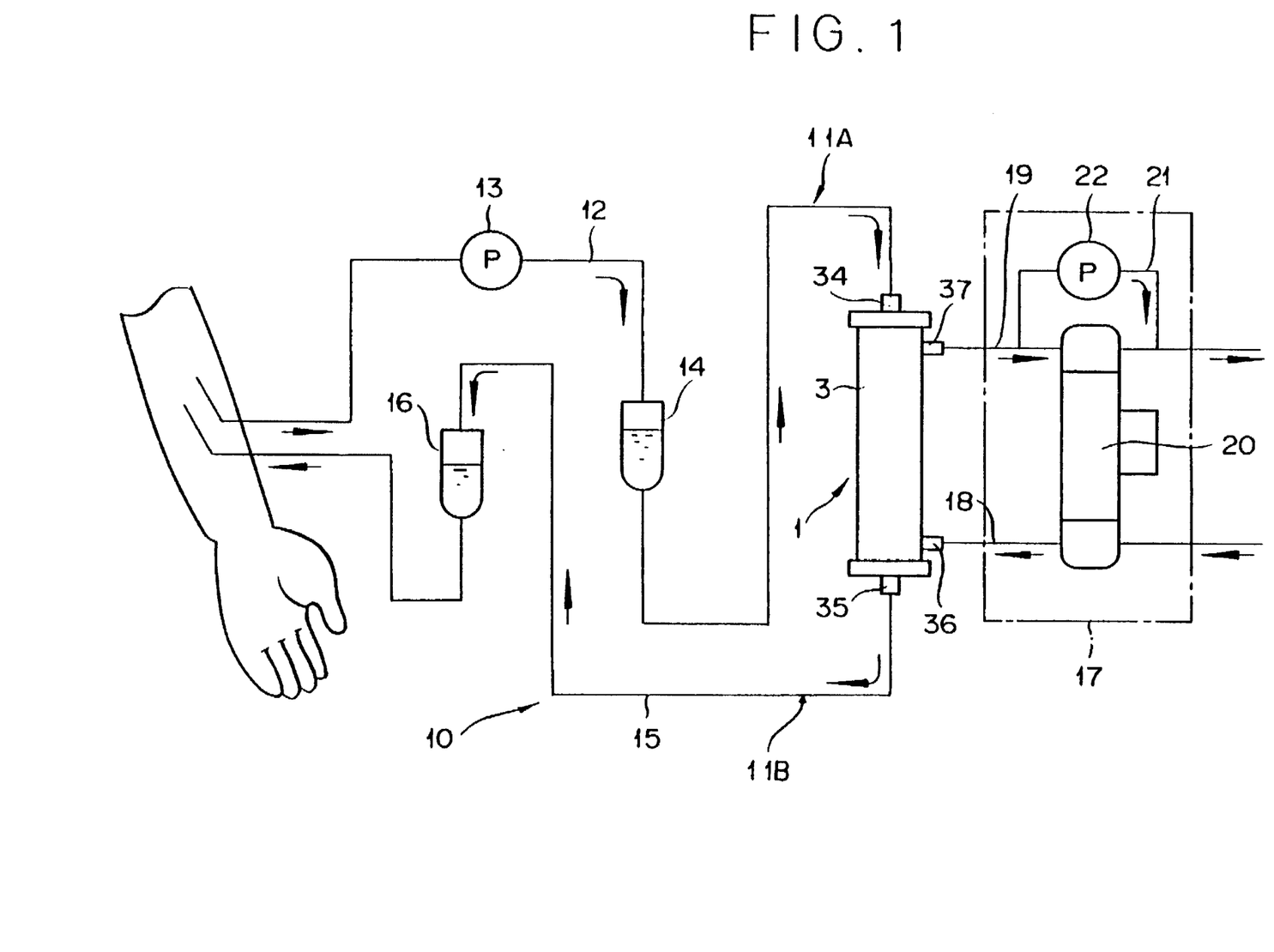
FIG. 1 is a circuit diagram showing an example of the construction of a circuit for extracorporeal blood circulation including a dialyzer according to this invention.

FIG. 1 is a circuit diagram schematically showing an example of the construction of a circuit for extracorporeal blood circulation including a dialyzer of this invention. As shown in this diagram a circuit 10 for extracorporeal blood circulation is provided with a blood extracting line 11A, a dialyzer 1, a blood returning line 11B, and UFR control means 17.

The blood extracting line 11A is composed of a tube 12, a pump 13 disposed halfway in the length of the tube 12 and used for forwarding blood, and a chamber 14 for depriving the blood of bubbles. The blood extracting line 11A is connected at one end thereof to the artery of a patient through the medium of a syringe and at the other end thereof to a blood inlet 34 to the dialyzer 1.

The blood returning line 11B is composed of a tube 15 and a chamber 16 disposed halfway in the length of the tube 15 and used for depriving the blood of bubbles. The blood returning line 11B is connected at one end thereof to the vein of a patient through the medium of a syringe and at the other end thereof to a blood outlet 35 of the dialyzer.

The UFR control means 17 is composed of a tube 18 connected at one end thereof to a dialyzing liquid inlet 36 of the dialyzer 1, a tube 19 connected at one end thereof to a dialyzing liquid outlet 37 of the dialyzer 1, a multiple pump 20 for delivering the dialyzing liquid at an equal flow volume in opposite directions into the tubes 18 and 19, a bypass tube 21 laid to bypass the multiple pump 20 and connected at the opposite ends thereof to the tube 19, and a filtration pump 22 disposed halfway in the length of the bypass tube 21.

Incidentally, a roller pump is preferably used for the pump 13 mentioned above.

The multiple pump 20 is so adapted as to convert the rotary motion of a pump into the reciprocating motion of a plunger and effect the introduction of the dialyzing liquid and the discharge of the spent dialyzing liquid alternately by the mechanism of a check valve.

The filtration pump 22 is so adapted as to convert the rotary motion of a motor into the reciprocating motion of a plunger and effect the discharge of the spent dialyzing liquid in one fixed direction from within the cylinder.

Now, the operation of the circuit 10 for extracorporeal blood circulation will be described below.

In consequence of the operation of the pump 13, the blood extracted from a patient is caused to flow through the blood extracting line 11A, put to temporary storage in the chamber 14 and deprived therein of bubbles, and then allowed to flow into the dialyzer 1 via the blood inlet 34. The blood flowing out of the blood outlet 35 is made to flow through the blood returning line 11B, put to temporary storage in the chamber 16 and deprived therein of bubbles, and returned to the patient.

Meanwhile, in consequence of the operation of the multiple pump 20, the dialyzing liquid supplied from a dialyzing liquid reservoir not shown in the diagram is made to flow inside the tube 18, introduced into a housing 3 of the dialyzer 1 via the dialyzing liquid inlet 36, caused to undergo dialysis and filtration with the blood through the medium of individual hollow fiber membranes 41 inside the housing 3 as described specifically hereinbelow, and discharged through the dialyzing liquid outlet 37. The dialyzing liquid thus discharged is conveyed through the tube 19 and recovered ultimately. When the filtration pump 22 is operated at a prescribed number of revolutions at this time, a difference corresponding to the amount of discharge of the filtration pump 22 is produced between the amount of the dialyzing liquid supplied to the dialyzer 1 and the amount of the dialyzing liquid recovered from the dialyzer 1 and this amount of difference represents the amount of water removed from the blood passing through the dialyzer 1. Thus, the amount of water to be removed can be adjusted by adjusting the number of revolutions (amount of discharge) of the filtration pump 22.

Figure 2:
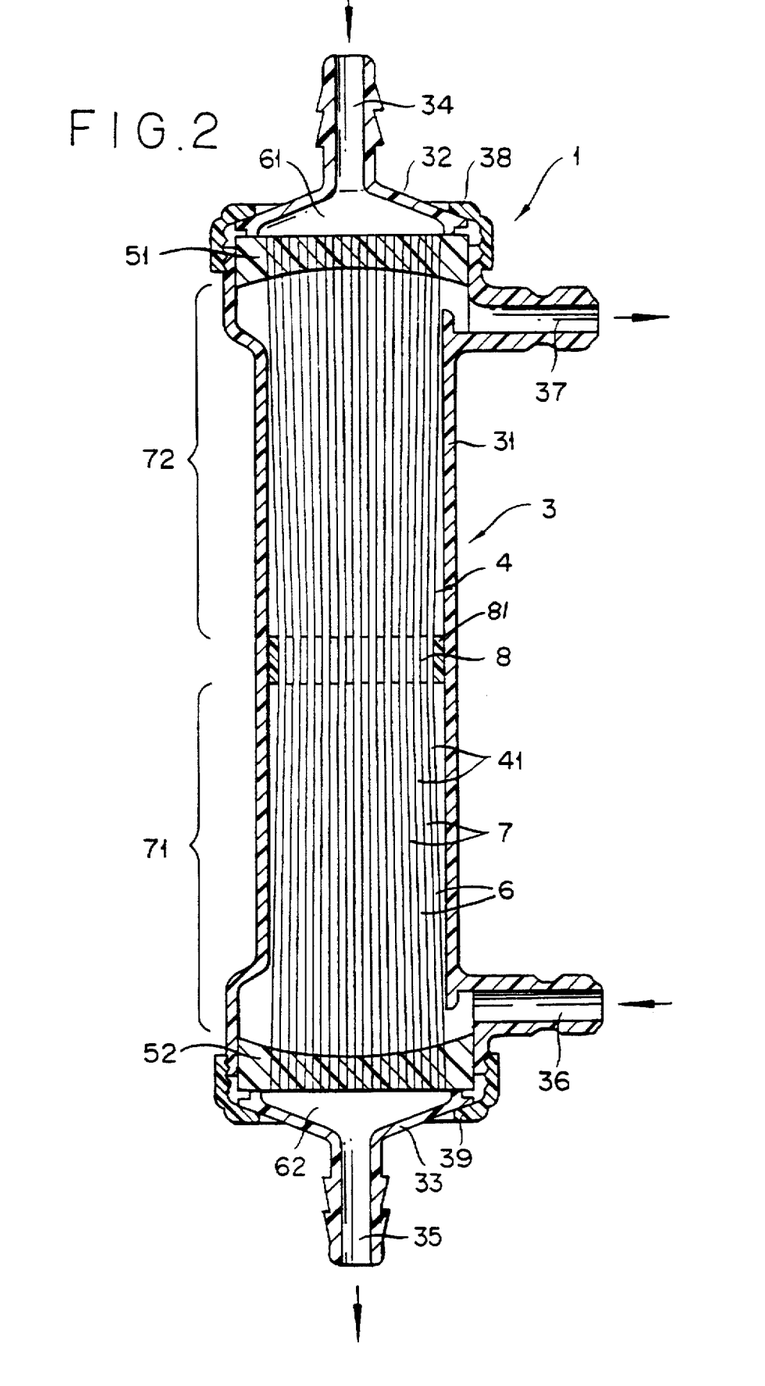
FIG. 2 is a longitudinal cross section showing the manner of embodying the dialyzer according to this invention.

FIG. 2 is a longitudinal cross section showing one embodiment of the dialyzer 1 of this invention. As shown in this diagram, the dialyzer 1 is provided with the housing 3 which is composed of a cylindrical main body 31 and headers 32 and 33 connected and fixed watertightly to the opposite ends of the cylindrical main body 31 respectively with covers 38 and 39. The blood inlet 34 is projected from the top of the header 32 and the blood outlet 35 is projected from the top of the header 33. The dialyzing liquid inlet 36 is projected from the lateral part of the cylindrical main body 31 on the header 33 side and the dialyzing liquid outlet 37 is projected from the lateral part of the cylindrical main body 31 on the header 32 side.

The cylindrical main body 31, the header 32 and 33, and the covers 38 and 39 are formed of hard resin such as, for example, polyethylene, polypropylene, polycarbonate, polymethyl methacrylate, acrylic type resins, hard polyvinyl chloride, styrene-butadiene copolymer resin, and polystyrene. They are preferably transparent or translucent to enable their interiors to be seen through discernibly. The header 32 and the header 33 may be dyed in different colors so as to facilitate distinction between the inlet side and the outlet side of the cylindrical main body 31.

The housing 3 has a bundle 4 of the hollow fiber membranes 41 accommodated therein throughout substantially the entire length thereof. In this case, the number of hollow fiber membranes 41 which form the bundle 4 is in the approximate range of from 100 to 70,000. The individual hollow fiber membranes 41 are arranged parallelly to one another as separated from one another and laid along the length of the housing 3.

As typical examples of the material for the hollow fiber membranes 41, regenerated cellulose, cellulose derivatives, polymethyl methacrylate, polyolefins such as polyethylene and polypropylene, polysulfones, polyacrylonitrile, polyamide, polyimide, polyether, silicone, polytetrafluoroethylene, and polyester polymer alloy may be cited.

Though the available membrane area of the whole hollow fiber membranes 41 is not specifically defined, it is preferably in the approximate range of from 100 $cm^2$ to 6.0 $m^2$, and more preferably in the approximate range of from 0.2 to 2.0 $m^2$.

The opposite end parts of the individual hollow fiber membranes 41 are watertightly supported and fixed in the end parts of the cylindrical main body 31 with the aid of partitions 51 and 52 in such a manner that the end part openings of the hollow fiber membranes 41 will not be plugged.

The partitions 51 and 52 are formed of such a potting material as, for example, polyurethane, silicone, or epoxy resin and they are produced by pouring the potting material in a liquid state by the centrifugal injection technique into the opposite end parts of the cylindrical main body 31 in the presence of the bundle 4 of the hollow fiber membranes 41 and allowing the injected potting material to cure.

A blood inflow chamber 61 is formed in the empty space which is surrounded by the header 32 and the partition 51 and a blood outflow chamber 61 is formed in the empty space which is surrounded by the header 33 and the partition 52. First flow paths (blood flow paths) 6 for the flow of blood are formed in the cavities (hollow parts) of the individual hollow fiber membranes 41. The opposite ends of the first flow paths 6 are made to communicate with the blood inflow chamber 61 and the blood outflow chamber 62.

In the cavity enclosed with the cylindrical main body 31 of the housing 3 and the two partitions 51 and 52, second flow paths (dialyzing liquid flow paths) 7 for the flow of the dialyzing liquid are formed in the gap between the bundle 4 of the hollow fiber membranes 41 and the inner wall surface of the cylindrical main body 31 and in the gap intervening between the adjacent hollow fiber membranes 41. In other words, the first flow paths 6 and the second flow paths 7 are separated by the individual hollow fiber membranes 41. The upstream sides of the second flow paths 7 communicate with the dialyzer liquid inlet 36 and the downstream sides thereof with the dialyzing liquid outlet 37.

Owing to the construction of the dialyzer described above, the blood which has flowed into the blood inflow chamber 61 via the blood inlet 34 is caused to flow through the first flow paths 6, gathered in the blood outflow chamber 62, and discharged through the blood outlet 35 and meanwhile the dialyzing liquid which has flowed in via the dialyzing liquid inlet 36 is caused to flow through the second flow paths 7 in the direction opposite to the flow of the blood mentioned above (counterflow) and flow out of the dialyzing liquid outlet 37.

A constricted part 8 for reducing the cross section of the second flow paths 7 is provided halfway along the length of the second flow paths 7 and is so adapted as to confer an expected difference of pressure on the dialyzing liquid flowing through the second flow paths 7 on an upstream side 71 of the dialyzing liquid and a downstream side 72 of the dialyzing liquid relative to the constricted part 8.

Figure 3:
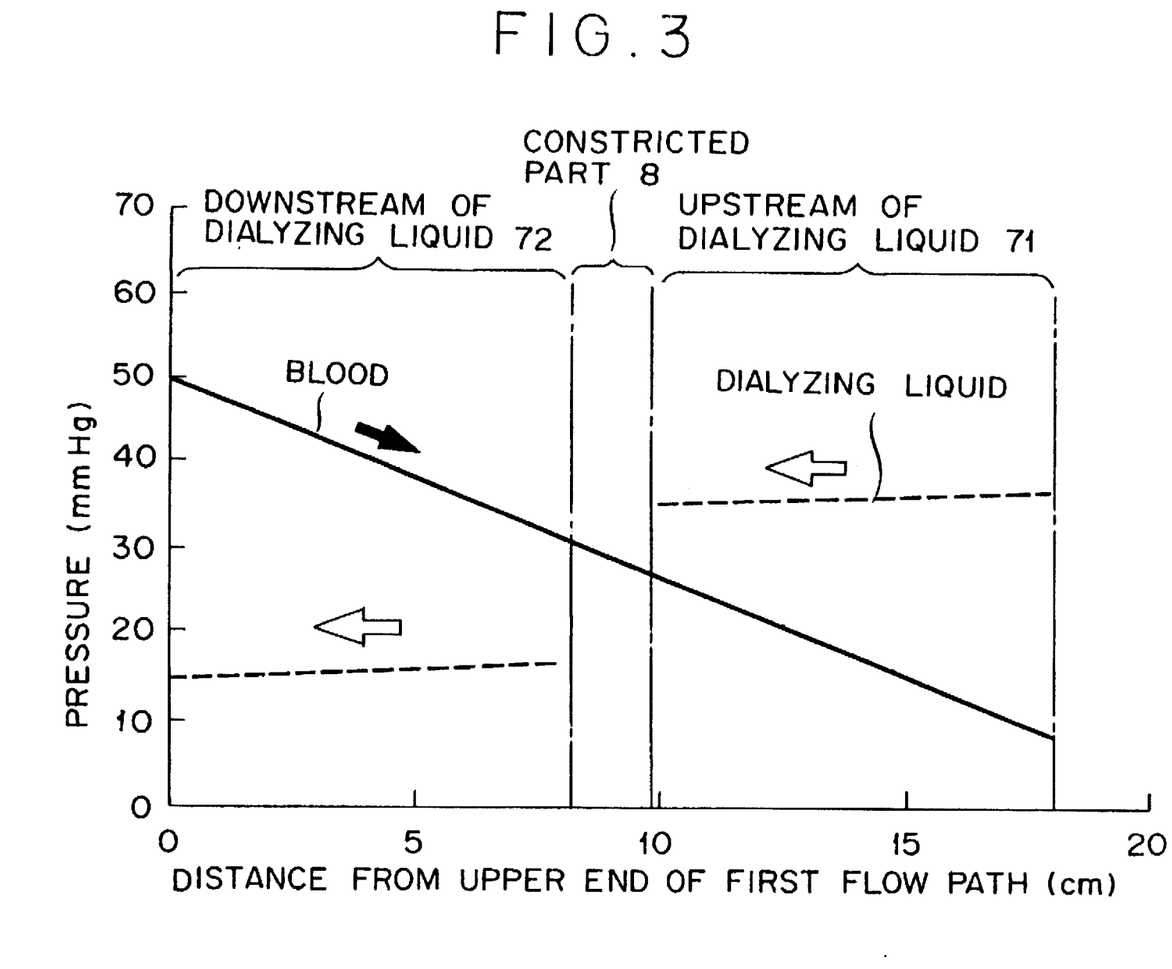
FIG. 3 is a graph showing the pressure distribution in the dialyzer.

FIG. 3 is a graph showing the pressure distribution in the blood flowing through the first flow paths 6 and in the dialyzing liquid flowing through the second flow paths. As shown in this diagram, the blood flowing through the first flow paths 6 has the pressure thereof decreased substantially linearly from the upstream to the downstream side and the dialyzing liquid flowing through the second flow paths 7 has the pressure thereof increased on the upstream side 71 of the dialyzing liquid relative to the constricted part 8 above the pressure of the blood at the corresponding position of the first flow paths 6 and decreased on the downstream side 72 of the dialyzing liquid relative to the constricted part 8 below the pressure of the blood at the corresponding position of the first flow paths 6.

The blood which flows through the first flow paths 6, therefore, first undergoes dialysis (diffusion of solute) and ultrafiltration (convection) through the medium of the individual hollow fiber membranes 41 on the downstream side 72 of the dialyzing liquid and subsequently undergo ultrafiltration (replenishment of liquid) from the dialyzing liquid side to the blood side through the medium of the individual hollow fiber membranes 41 on the upstream side 71 of the dialyzing liquid.

Since the replenishment of liquid is effected on the upstream side 71 of the dialyzing liquid, namely on the downstream side of the blood, as described above, the amount of the blood to be filtered from the blood side to the dialyzing liquid side can be increased on the upstream side of the blood and, as a result, the mass displacement of the blood and the dialyzing liquid can be realized. Moreover, this mass displacement can be implemented solely by the dialyzer 1 without additionally requiring use of any special device.

Preferably in this case, the ratio of ultrafiltration (coefficient of filtration of pure water) in the dialyzer 1 is not less than 20 ml/m$^2$.hr.mmHg when the flow volume of water is 200 ml/min and not less than 30 ml/m$^2$.hr.mmHg when the flow volume of water is 300 ml/min.

The constricted part 8 described above is formed, for example, by causing a constricted part-forming member 81 to intervene between the periphery of the bundle 4 of the hollow fiber membranes 41 and the inner wall surface of the cylindrical main body 31 of the housing 3 or by causing the constricted part-forming member 81 to fill the gap intervening between the adjacent hollow fiber membranes 41. Optionally, these two methods may be simultaneously used.

When the constricted part-forming member 81 is made to fill the gap between the adjacent hollow fiber membranes 41, the distribution of the constricted part-forming member 81 in the direction of the cross section of the bundle 4 may be uniform or ununiform (dense in the central part of the bundle 4 or coarse in the peripheral part thereof or vice versa, for example).

As typical examples of the material usable in this case for the constriction part-forming member 81, (cross-linked) polyacrylic salts or (cross-linked) acrylic acid-acrylic salt copolymers (proprietary products such as, for example, AQUALIC of Nippon Shokubai Co., Ltd., ARASORB of Arakawa Kagaku Kogyo K. K., WONDERGEL of Kao Co., Ltd., AQUAKEEP of Seitetsu Kagaku Co., Ltd., D.W.A.L. of The Dow Chemical Company, PARMASORB of National Starch Company, and FAVOR of Stockhausen), isobutylene-maleic acid copolymers (proprietary products such as, for example, KI Gel of Kuraray Isoprene Co., Ltd.), starch-acrylic acid graft copolymers or saponification derivatives thereof (proprietary products such as, for example, SAN-WET of Sanyo Chemical Industries Co., Ltd., GPC of Grain Processing Company, SGP of Henkel Company, Magic Water Gel of Super Absorbent Company, and LYOGEL of Unilever Company), saponified vinyl acetate-acrylate copolymers (proprietary products such as, for example, SUMIKAGEL of Sumitomo Chemical Co., Ltd.), vinyl acetate-unsaturated dicarboxylic acid copolymers (proprietary products such as, for example, GP of Nippon Synthetic Chemical Industry Co., Ltd), carboxy methyl cellulose (proprietary products such as, for example, CLD of Buckeye Cellulose Corp and AKUCELL of Enka Corp), alginates (proprietary products such as, for example, CECAGUM of CECA Corp), and composite fibers formed of a core of acrylonitrile fiber and a coat of an acrylate copolymer (proprietary products such as, for example, LANSEAL of Toyo Spinning Co., Ltd.) may be cited.

Among other materials cited by way of example above, the composite fibers formed of a core of acrylonitrile fiber and a coat of an acrylic salt copolymer prove most suitable. Information on the ultra-absorbent fibers is found in a catalog of Toyo Spinning Co., Ltd. titled "LANSEAL, ultra-absorbent fibers."

When the constricted part-forming member 81 to be used is made of a resin, the constricted part 8 can be formed by partially filling the gap between the periphery of the bundle 4 and the inner wall surface of the cylindrical main body 31 and the gap between the adjacent hollow fiber membranes 41 with the resin. When the constricted part-forming member 81 is made of fibers, the constricted part 8 can be formed by winding the fibers or an aggregate thereof around the bundle 4 or knitting the fibers or the aggregate thereof through the gap between the adjacent hollow fiber membranes 41. Optionally, the fibers may be impregnated with a resin and solidified.

The bundle 4 may be split into a plurality of bundles and the constricted part-forming member 81 may be disposed in the same manner as described above to form the constricted part 8 on each of the split bundles.

In the dialyzer according to this invention, the packing ratio of the hollow fiber membranes in the constricted part is in the range of from 105 to 200%, preferably from 120 to 180%, based on the packing ratio in the parts other than the constricted part. If the packing ratio is less than 105%, difference of the pressure between upstream side and downstream side is small, so it is difficult to substitute of the liquid effectively, and if the packing ratio exceeds 200%, there is possibility that the hollow fiber membrancees are pressed.

By reason of convenience of manufacture, the constriction part-forming member 81 is appropriately made of a material which possesses the property of being swelled with dialyzing liquid (dialyzing liquid-absorption capacity). The dialyzing liquid-absorption capacity of this material is in the range of at least 10% by weight, preferably from 10 to 2,600% by weight, and more preferably from 50 to 2,000% by weight. It is the dialyzing liquid and not water that is absorbed by the dialyzing liquid-material in the dialyzer. The dialyzing liquid is known in numerous kinds. The different kinds thereof have water-absorption capacities more or less different from one another. Although dialyzing liquid-absorption capacity of the dialyzing liquid swellable material is influenced by ion strength of electiolites in a solution, there is little difference of mono- and divalent ion concentrations in the dialyzing liquid generally used, so change of weight increasing ratio is low even if the dialyzing liquid changes.

Compositions of the typical dialyzing liquids are shown in Table 1. The water-absorption capacity of a given dialyzing liquid, is determined, therefore, by actually measuring the absorption ratio on the basis of ion strength and reducing this absorption capacity to that of water.

The relation between the amount of dialyzing liquid-swellable material to be used and the dialyzing liquid-absorption capacity thereof is expressed by the following formula.

$$\frac{19 \times \pi}{20 \times 2 \times 2} \rho \left( D_h^2 - \frac{9}{7} D_0^2 N \right) l \leq \left( 1 + \sqrt{\frac{H}{100}} \right) m \leq$$

$$\frac{1}{2} \pi \rho (D_h^2 - D_0^2 N) l$$

wherein $\rho$ is a density of dialyzing liquid, $D_h$ is an inside diameter of the housing, $D_o$ is an outside diameter of the hollow fiber membrane, N is an number of hollow fiber membranes, l is a length of the constricted part, H is a dialyzing liquid-absorption capacity [(M'−m')/m']×100, M' is a weight of the dialyzing liquid-swellable material in the state swelled with dialyzing liquid, m' is a weight of the dialyzing liquid-swellable material in the dried state and m is a weight of the dialyzing liquid-swellable material.

Incidentally, the relation between the length, l, of the constricted part and the available length, L, of the module is expressed as follows.

$$l/L \leq \frac{1}{3}$$

The method for incorporating the dialyzing liquid-swellable material and the method for applying the swelling resin are shown below.

(a) Method for incorporating the dialyzing liquid-swellable fiber

A bundle of hollow fiber membranes is obtained by preparing warps or wefts each formed of a bundle of up to some tens of hollow fibers and wefts or warps of dialyzing liquid-swellable fibers, weaving the warps and the wefts to the extent of causing the central parts of hollow fiber membranes to be interlaced in a fixed width (length of not more than ⅓ of the available lengths of hollow fibers), and rolling the resultant weave around the ends of dialyzing liquid-swellable fibers having the central parts of hollow fiber membranes knit therein after the fashion of a reed screen in such a manner as to contain the reed screen in the finished roll.

(b) Method for applying swellable resin

A bundle of hollow fiber membranes is formed of a bundle of up to some tens of hollow fiber membranes, spreading the bundle of hollow fiber membranes unidirectionally, applying a dialyzing liquid-swellable member to the central parts of the hollow fiber membranes covering a fixed width (length of not more than ⅓ of the available length of hollow fibers), allowing the applied dialyzing liquid-swellable resin to dry or cure, and rolling the resultant the spreaded bundles around one end of the dialyzing liquid-swellable resin coat after the fashion of a reed screen.

The average of the pressure difference (pressure loss) on the upstream side 71 and the downstream side 72 of the dialyzing liquid relative to the constricted part 9 is appropriately in the approximate range of from 10 to 100 mmHg, preferably from 30 to 70 mmHg. The observance of this specific range allows the mass displacement of blood and the dialyzing liquid to be carried out efficiently. The material of the constricted part-forming member 81 for the constricted part 8, the density of distribution, the area of distribution, and the like are suitably adjusted so as to obtain the pressure difference specified above.

Though the position for forming the constricted part 8 in the second flow paths is not specifically limited, it is preferably such that the ratio of the length of flow path of the dialyzing liquid on the upstream side 71 to the length of flow path of the dialyzing liquid on the upstream side 72 falls in the approximate range of from 2:1 to 1:2. The observance of this specific range allows the mass displacement of blood and the dialyzing liquid to be effected efficiently. In the construction illustrated by way of example, the constricted part 8 is formed in the central part in the direction of length of the second flow paths so that the length of flow paths on the upstream side 71 and the length of flow paths on the downstream side 72 of the dialyzing liquid is practically equal.

In this invention, the construction of the constricted part 8, the method for formation thereof, the characteristics thereof, and the like are not limited to those described above. They are only required to be such as to confer the difference of pressure on the dialyzing liquid on the upstream side and the downstream side of the dialyzing liquid relative to the constricted part.

Though the embodiment described above concerns the use of the dialyzer 1 for the treatment of blood, the body liquid to be treated thereby may be a blood component such as, for example, blood plasma instead.

Now, the dialyzer of this invention will be described in detail below with reference to working examples.

EXAMPLE 1

A bundle of about 5,000 polysulfone hollow fiber membranes having an outside diameter of 280 μm and an inside diameter of 200 μm (having an available membrane area of 0.5 m²) was prepared. A total of 2 g of dialyzing liquid-absorbent fibers made of composite fibers comprising an acrylonitrile fiber inner layer and an acrylate copolymer outer layer [produced by Toyo Spinning Co., Ltd. and marketed under trademark designation of "LANSEAL F," having a dialyzing liquid-absorption capacity of 1,963%] were wound around the periphery of the bundle in the central part thereof in the direction of length over a width of 2 cm. Then, this bundle of hollow fiber membranes was inserted into a cylindrical main body of polycarbonate having an available length of 175 mm and an inside diameter of 30 mm and provided with an inlet and an outlet for the dialyzing liquid in such a manner as to avoid occurrence of a gap between the absorbent fibers and the cylindrical main body.

Subsequently, a potting material of polyurethane was injected into the opposite end parts of hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet Were attached severally to the opposite end parts of the cylindrical main body and watertightly fixed thereto by fusion to obtain a dialyzer of the construction shown in FIG. 2.

Control 1

The same bundle of about 5,000 polysulfone hollow fiber membranes (available membrane area 0.5 $m^2$) as used in Example 1 was inserted into a cylindrical main body provided with an inlet and an outlet for a dialyzing liquid. Then, a potting material was injected into the opposite end parts of the individual hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer.

The available length and the inside diameter of the cylindrical main body were 175 mm and 30 mm respectively.

EXAMPLE 2

A bundle of about 11,000 polysulfone hollow fiber membranes identical to those used in Example 1 (available membrane area 1.6 $m^2$) was prepared. A total of 2 g of the same absorbent fibers (dialyzing liquid absorption capacity 1,963) as used in Example 1 were wound around the periphery of the bundle in the central part in the direction of length thereof over a length of 2 cm. The bundle of hollow fiber membranes was inserted into a cylindrical main body provided with an inlet and an outlet for a dialyzing liquid in such a manner as to avoid occurrence of a gap between the absorbent fibers and the inner wall surface of the cylindrical main body.

Subsequently, a potting material was injected into the opposite end parts of hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer of the construction shown in FIG. 2.

The available length and the inside diameter of the cylindrical main body were 235 mm and 39 mm respectively.

Control 2

The results of the process for on-line dialysis and filtration (pre-dilution method) published in the prior literature [Kenichi Murayama et al.: "Nephros and Dialysis," Vol. 34, extra issue titled "High Performance Membrane," 93, P117 (1993)] are cited. These results are shown in Table 2 below. The available membrane area of the dialyzer was 1.6 $m^2$, a magnitude identical to that of Example 1.

The molecular weight of $\beta_2$ microglobulin, the solute to be removed in Control 2, was 11,800. Since it approximates the molecular weight, 12,400, of cytochrome mentioned above, the module of dialysis and filtration of identical performance is believed to exhibit practically the same clearance value.

EXAMPLE 3

A bundle of about 4,000 polyamide hollow fiber membranes each having an outside diameter of 335 μm and an inside diameter of 215 μm (available membrane area 0.4 $m^2$) was prepared. A total of 2 g of the same absorbent fibers (dialyzing liquid absorption capacity 1,963%) as used in Example 1 were wound around the periphery of the bundle in the central part in the direction of length thereof over a length of 2 cm. This bundle of hollow fiber membranes was inserted into a cylindrical main body provided with an inlet and an outlet for a dialyzing liquid in such a manner as to avoid occurrence of a gap between the absorbent fibers and the inner wall surface of the cylindrical main body.

Subsequently, a potting material was injected into the opposite end parts of hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer of the construction shown in FIG. 2.

The available length and the inside diameter of the cylindrical main body were 175 mm and 30 mm respectively.

Control 3

A bundle of about 4,000 polyamide hollow fiber membranes (available membrane area 0.4 $m^2$) was inserted into a cylindrical main body provided with an inlet and an outlet for a dialyzing liquid. Then, a potting material was injected into the opposite end parts of the individual hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer. The available length and the inside diameter of the cylindrical main body were 175 mm and 30 mm respectively.

EXAMPLE 4

A bundle of about 6,000 polyamide hollow fiber membranes identical to those used in Example 3 (available membrane area 0.7 $m^2$) was prepared. A total of 3 g of cellulose resin (dialyzing liquid absorption capacity 50%) was applied to the periphery of the bundle in the central part in the direction of length thereof over a width of 2 cm and dried. The bundle of hollow fiber membranes was inserted into a cylindrical main body provided with an inlet and an outlet for a dialyzing liquid.

Subsequently, a potting material was injected into the opposite end parts of hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer of the construction shown in FIG. 2.

The available length and the inside diameter of the cylindrical main body were 175 mm and 30 mm respectively.

Control 4

A bundle of about 6,000 polyamide hollow fiber membranes (available membrane area 0.7 m$^2$) was inserted into a cylindrical main body provided with an inlet and an outlet for a dialyzing liquid. Then, a potting material was injected into the opposite end parts of the individual hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer. The available length and the inside diameter of the cylindrical main body were 175 mm and 30 mm respectively.

EXAMPLE 5

A bundle of polyacrylonitrile hollow fiber membranes (available membrane area 0.6 m$^2$) each having an outside diameter of 305 μm and an inside diameter of 245 μm was prepared. Urethane resin (dialyzing liquid absorption capacity of about 10%) was applied in the form of a layer to the periphery of the bundle in the central part in the direction of length thereof and, at the same time, about 3 g of the same urethane resin was partially packed on the inner part of the bundle to fill the gap between the adjacent hollow fiber membranes over a length of 1 cm. This bundle of hollow fiber membranes was inserted into a cylindrical main body provided with an inlet and an outlet for a dialyzing liquid in such a manner as to reduce the gap between the layer of urethane resin and the inner wall surface of the cylindrical main body.

Subsequently, a potting material was injected into the opposite end parts of hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer of the construction shown in FIG. 2.

The available length and the inside diameter of the cylindrical main body were 175 mm and 30 mm respectively.

Control 5

The same bundle of about 4,500 polyacrylonitrile hollow fiber membranes (available membrane area 0.6 m$^2$) as used in Example 1 was inserted into a cylindrical main body provided with an inlet and an outlet for a dialyzing liquid. Then, a potting material was injected into the opposite end parts of the individual hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer.

The available length and the inside diameter of the cylindrical main body were 175 mm and 30 mm respectively.

EXAMPLE 6

The dialyzers of Examples 1 through 5 and Controls 1 through 5 were each set in place in a circuit for extracorporeal blood circulation shown in FIG. 1 and subjected to an in vitro experimental dialysis using cytochrome C (molecular weight=12,400) in accordance with the standard for rating an artificial kidney set by Japanese Society for Artificial Organs for Artificial Organs.

A dialyzing liquid containing 40% of glycerol was used as a solution on the blood side. The amount of water removed (flow volume of dialysis) was fixed at 10 ml/min. In consequence of the flow of the dialyzing solution liquid, the absorbent fibers or the dialyzing liquid-swellable material was swelled to give rise to a constricted part in the part of the bundle on which the absorbent fibers were wound or to which the dialyzing liquid-swelling material was applied. The results of the test are shown in Table 2.

TABLE 1

| | mEq/l | | | | | | acetate | glucose |
|---|---|---|---|---|---|---|---|---|
| | Na | K | Ca | Mg | Cl | HCO$_3$ | (lactic acid) | (mg/dl) |
| Kolff | 138 | 3.5 | 5.0 | 1.5 | 112 | 36 | | 500 |
| Kinderly No. 1 | 134 | 2.6 | 2.5 | 1.5 | 104 | | 36.6 | 554.5 |
| Kinderly No. 2 | 132 | 2.0 | 2.5 | 1.5 | 105 | | 33.0 | 200 |
| Kinderly No. 3 | 132 | 2.0 | 3.5 | 1.5 | 104 | | 35.0 | 200 |
| Kinderly GF | 135 | 2.0 | 3.75 | 1.5 | 105.25 | | 37.0 | — |
| Kinderly Na 140 | 140 | 2.0 | 3.3 | 1.0 | 109.3 | | 37.0 | 100 |
| AK Soklta | 132 | 2.0 | 2.5 | 1.5 | 105 | | 33.0 | 200 |

TABLE 2

| | Amount of ultrafiltration (ml/m²/hr/mmHg) | Cross-sectional area of cylindrical main body (mm²) | Total area of hollow fiber membranes (mm2) | Packing ratio in parts other than constricted part (%) | Packing ratio in constricted part (%) | Ratio of constricted part to other part (%) | Pressure difference of dialyzing liquid (mmHg) | Clearance (ml/min) | Amount of displacement during 3 hour's circulation (liter) |
|---|---|---|---|---|---|---|---|---|---|
| Example 1 | 128.0 | 706.9 | 307.9 | 43.6 | 78 | 179 | 56 | 47 | 4.0 |
| Control 1 | 128.0 | 706.9 | 307.9 | 43.6 | 43.6 | 100 | 3 | 36 | 2.0 |
| Example 2 | | 1,194.6 | 677.3 | 56.7 | 78 | 138 | 62 | 109 | 18 |
| Control 2 | | 1,194.6 | 677.3 | 56.7 | 56.7 | 100 | — | 80–92 | 36–54 |
| Example 3 | 376.4 | 706.9 | 352.6 | 49.9 | 78 | 156 | 60 | 29 | — |
| Control 3 | 376.4 | 706.9 | 352.6 | 49.9 | 49.9 | 100 | 3 | 7 | — |
| Example 4 | | 706.9 | 528.8 | 74.8 | 78 | 104 | 20 | 17 | — |
| Control 4 | | 706.9 | 528.8 | 74.8 | 74.8 | 100 | 3 | 13 | — |
| Example 5 | 263.4 | 706.9 | 328.8 | 46.5 | 78 | 168 | 60 | 46 | 3.6 |
| Control 5 | 263.4 | 706.9 | 328.8 | 46.5 | 46.5 | 100 | 4 | 34 | 2.0 |

As shown in Table 2, the clearance value of cytochrome C (the amount of a solution on the blood side for which the concentration of cytochrome C in 200 ml of a solution on the blood side reaches 0) obtained by the dialyzer of Example 1 was higher by 11 ml/min than that obtained by the dialyzer of Control 1, indicating that the performance of the former dialyzer was notably high as compared with that of the latter dialyzer.

It is clearly noted from Table 2 that the clearance value obtained by the dialyzer of Example 2 was higher than that obtained by the dialyzer of Control 2. This fact indicates that the use of the dialyzer of Example 2 permits therapeutic dialysis to be effected with high efficiency by simply controlling the removal of water as popularly practiced without requiring use of any extra device for predilution.

As shown in Table 2, the clearance value of cytochrome C obtained by the dialyzer of Example 3 was more than four times as high as that obtained by the dialyzer of Control 1, indicating that the performance of the former dialyzer was notably high as compared with that of the latter dialyzer.

It is clear from Table 2 that the clearance value of cytochrome C obtained by the dialyzer of Example 3 was higher by 4 ml/ml than that obtained by the dialyzer of Control 4, indicating that the performance of the former dialyzer was notably high as compared with that of the latter dialyzer.

It is clear from Table 2 that the clearance value of cytochrome C obtained by the dialyzer of Example 4 was higher by 12 ml/ml than that obtained by the dialyzer of Control 5, indicating that the performance of the former dialyzer was notably high as compared with that of the latter dialyzer.

EXAMPLE 7

A bundle of about 6,000 polyamide hollow fiber membranes having an outside diameter of 335 μm, an available membrane area of 0.7 m², and UFR=62.9 ml/m²/hr/mmHg was prepared. A total of 2 g of the same absorbent fibers (having a dialyzing liquid absorption capacity of 1,963%) as used in Example 1 were wound around the periphery of the bundle over a length of 2 cm. The bundle was inserted into a cylindrical main body having an available length of 175 mm and an inside diameter of 32 mm and provided with an inlet and an outlet for a dialyzing liquid.

Subsequently, a potting material was injected into the opposite end parts of hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer of the construction shown in FIG. 2.

Control 6

A dialyzer was obtained by following the procedure of Example 7 while inserting the bundle of hollow fiber membranes into a cylindrical main body provided with an inlet and an outlet for a dialyzing liquid and possessed of a constricted part in the central part thereof (the inside diameter of the constricted part 29.5 mm, the width of the constricted part 20 mm, the inside diameter of the main body other than the constricted part 32 mm, and the available length of main body 175 mm).

EXAMPLE 8

The dialyzers of Example 7 and Control 6 were each set in place in a circuit for extracorporeal blood circulation shown in FIG. 1 and subjected to an in vitro experimental dialysis using $\beta_2$-microglobulin ($\beta_2$-MG, molecular weight= 11,800) in accordance with the standard for rating an artificial kidney set by Japanese Society for Artificial Organs.

A human blood serum (total protein concentration 6.5 g/dl) was used as a solution on the blood side. The amount of water removed (flow volume of dialysis) was fixed at 10 ml/min. The results of this test are shown in Table 3.

TABLE 3

| | Pressure difference of dialyzing liquid (mmHg) | CL($\beta_2$-MG) (ml/min) | Packing ratio in parts other than constricted part (%) | Packing ratio in constricted part (%) |
|---|---|---|---|---|
| Example 7 | 70 | 29.7 | 65.8 | 78 |
| Control 6 | 7 | 13.2 | 65.8 | 77.4 |

EXAMPLE 9

A bundle of about 10,000 polysulfone hollow fiber membranes having an outside diameter of 280 μm, an available membrane area of 15 m², and UFR=46.0 ml/m²/hr/mmHg was prepared. A total of 2 g of the same absorbent fibers (having a dialyzing liquid absorption capacity of 1,963%) as used in Example 1 were wound around the periphery of the bundle over a length of 2 cm. The bundle was inserted into a cylindrical main body having an available length of 235 mm and an inside diameter of 32 mm and provided with an inlet and an outlet for a dialyzing liquid.

Subsequently, a potting material was injected into the opposite end parts of hollow fiber membranes inserted in the cylindrical main body and allowed to cure to fix the individual hollow fiber membranes in position. The opposite ends of the cured plugs of potting material were sliced to open the individual hollow fiber membranes. A cover fitted with a blood inlet and a cover fitted with a blood outlet were attached severally to the opposite end parts of the cylindrical main body and watertightly fixed thereto by fusion to obtain a dialyzer of the construction shown in FIG. 2.

Two dialyzers of Example 9 were prepared. One of them was set in place in the circuit for extracorporeal blood circulation shown in FIG. 1 counter flow and the other in a parallel flow circuit and were subjected to an in vitro experimental dialysis using $\beta_2$-microglobulin ($\beta_2$-MG, molecular weight 11,800) in accordance with the standard for rating an artificial kidney set by Japanese Society for Artificial Organs.

A heparinized bovine blood (prepared with physiological saline solution to a hematocrit of 30% and a total protein concentration of 6.5 g/dl and containing $\beta_2$-MG) was used as a solution on the blood side. The amount of water removed (flow volume of dialysis) was fixed at 10 ml/min.

|  | CL ($\beta_2$-MG) ml/min |
| --- | --- |
| Counter flow | 93.0 |
| Parallel flow | 73.2 |

The results in the parallel flow were nearly the same as those in the counterflow.

The dialyzer of this invention, as described above, has the constricted part formed midway in the length of the second flow paths for the flow of the dialyzing liquid so as to confer a prescribed difference of pressure on the dialyzing liquid on the upstream side and the downstream side of the dialyzing liquid relative to the constricted part. The sole use of this dialyzer, therefore, permits mass displacement between the body liquid under treatment and the dialyzing liquid to be effected with improved performance in dialysis and filtration without requiring additional use of a special device.

Particularly when the dialyzer is so adapted that the pressure of the dialyzing liquid flowing through the second flow paths is higher than the pressure of the body liquid flowing through the first flow paths on the upstream side of the dialyzing liquid relative to the constricted part and the pressure of the dialyzing liquid flowing through the second flow paths is lower than the pressure of the body liquid flowing through the first flow paths on the downstream side of the dialyzing liquid relative to the constricted part, the mass displacement mentioned above is efficiently carried out with notable improvement of the performance in dialysis and filtration because the filtration from one to the other of the body liquid and the dialyzing liquid and the filtration in the reverse direction are carried out before and after the constricted part inside one dialyzer.

When the constricted part is formed by causing the constricted part-forming member to intervene between the periphery of the bundle of hollow fiber membranes and the inner wall surface of the housing or to fill the gap between the adjacent hollow fiber membranes, the formation thereof is attained easily and the pressure characteristics mentioned above can be obtained stably.

When the constricted part-forming member is made of a dialyzing liquid-swellable material particularly having a dialyzing liquid absorption capacity of not less than 10%, the bundle of hollow fiber membranes can be easily inserted into the housing and, owing to the swelling of the constricted part in consequence of the flow therethrough of the dialyzing liquid while the dialyzer is in use, can be made to adhere fast to the housing.

When the dialyzer incorporates therein UFR control means capable of adjusting the amount of water to be removed from the body liquid flowing through the first flow paths, the pressure characteristics mentioned above and the amount of water to be removed can be appropriately set to suit the particular case of disease.

What is claimed is:

1. A dialyzer comprising a cylindrical housing in which is positioned a bundle of hollow fiber membranes, first flow paths and second flow paths separated from each other by said hollow fiber membranes for effecting dialysis and ultrafiltration through the medium of said hollow fiber membranes between a body liquid flowing through said first flow paths and a dialyzing liquid flowing through said second flow paths, a body liquid inlet and body liquid outlet in fluid communication with the first flow paths, a dialyzing liquid inlet and a dialyzing liquid outlet in fluid communication with the second flow paths, and a constricted part formed halfway along the length of said second flow paths with a material capable of being swelled by said dialyzing liquid so as to confer a difference of pressure on said dialyzing liquid on an upstream side and a downstream side of said dialyzing liquid relative to said constricted part.

2. A dialyzer according to claim 1, wherein the pressure of said dialyzing liquid flowing through said second flow paths is so set as to be higher than that of said body liquid flowing through said first flow paths on the upstream side of said dialyzing liquid relative to said constricted part and the pressure of said dialyzing liquid flowing through said second flow paths is so set as to be lower than that of said body liquid flowing through said first flow paths on the downstream side of said dialyzing liquid relative to said constricted part.

3. A dialyzer according to claim 1, wherein said bundle of hollow fiber membranes possesses a periphery and the housing possesses an inner wall, said constricted part being formed by a constricted part-forming member intervening between the periphery of the bundle of said hollow fiber membranes and the inner wall surface of said housing.

4. A dialyzer according to claim 1, wherein said constricted part is formed by a constricted part-forming member that fills a gap between adjacent hollow fiber membranes.

5. A dialyzer according to claim 1, wherein said material capable of being swelled by said dialyzing liquid has a dialyzing liquid absorption capacity of not less than 10%.

6. A dialyzer according to any of claims 2 through 5, including an ultrafiltration rate control means connected to the dialyzing liquid inlet and the dialyzing liquid outlet for adjusting the amount of water to be removed from the body liquid flowing through said first flow path.

7. A dialyzer according to claim 3, wherein said constricted part-forming member is formed of dialyzing liquid-swellable fibers.

8. A dialyzer according to claim 1, wherein said hollow fiber membranes possess a packing ratio in said constricted part in a range of from 105 to 200% based on the packing ratio in parts other than said constricted part.

\* \* \* \* \*

UNITED STATES PATENT AND TRADEMARK OFFICE
CERTIFICATE OF CORRECTION

PATENT NO. : 5,700,372
DATED : December 23, 1997
INVENTOR(S) : Shingo TAKESAWA et al It is certified that error appears in the above-identified patent and that said Letters Patent is hereby corrected as shown below:

On the title page, and col. 1, line 3, delete "DIALIZING" and insert --DIALYZING--

In Section [56], kindly add "4,140,637, 2/1979 Walter".

In Column 1, line 52, delete "Japan Patent - 56-22,911--.

-- JUM-B-56-22,911 --.

In Column 6, line 3, delete "ml/m².hr.mmHg" and insert -- ml/m²·hr·mmHg --.
In Column 6, line 4, delete "ml/m².hr.mmHg" and insert -- ml/m²·hr·mmHg --.
In Column 7, line 51, delete "l" and insert -- $\ell$ --.
In Column 7, line 57, delete "l" and insert -- $\ell$ --.
In Column 9, line 21, delete "Were" and insert -- were --.

Signed and Sealed this

Nineteenth Day of May, 1998

Attest:

BRUCE LEHMAN

*Attesting Officer*  *Commissioner of Patents and Trademarks*